(12) United States Patent
Chelak et al.

(10) Patent No.: US 10,368,789 B2
(45) Date of Patent: Aug. 6, 2019

(54) MEDICAL PORT WITH CONSTRAINING BIASING ELEMENT

(71) Applicant: NP Medical Inc., Clinton, MA (US)

(72) Inventors: Todd Chelak, Westborough, MA (US); Ian Kimball, Townsend, MA (US); Ray Adams, Ansonia, CT (US); Jeffrey Ransden, Fairfield, CT (US)

(73) Assignee: NP MEDICAL INC., Clinton, MA (US)

( * ) Notice: Subject to any disclaimer, the term of this patent is extended or adjusted under 35 U.S.C. 154(b) by 96 days.

(21) Appl. No.: 15/389,977

(22) Filed: Dec. 23, 2016

(65) Prior Publication Data

US 2018/0177444 A1 Jun. 28, 2018

(51) Int. Cl.
*A61B 5/15* (2006.01)
*A61B 5/0215* (2006.01)
(Continued)

(52) U.S. Cl.
CPC ...... *A61B 5/150221* (2013.01); *A61B 5/0215* (2013.01); *A61B 5/02152* (2013.01);
(Continued)

(58) Field of Classification Search
CPC ............ A61B 5/150221; A61B 5/0215; A61B 5/150992; A61M 39/04
See application file for complete search history.

(56) References Cited

U.S. PATENT DOCUMENTS 4,936,542 A 6/1990 Beard
5,098,405 A 3/1992 Peterson et al.
(Continued)

FOREIGN PATENT DOCUMENTS

EP 0 247 425 A2 12/1987
EP 1 234 596 A1 8/2002
(Continued)

OTHER PUBLICATIONS

European Patent Office, International Search Report—Application No. PCT/US2014/058234, dated Dec. 16, 2014, including the Written Opinion of the International Searching Authority (10 pages).
(Continued)

*Primary Examiner* — Rebecca E Eisenberg
*Assistant Examiner* — Tasnim Mehjabin Ahmed
(74) *Attorney, Agent, or Firm* — McCarter & English, LLP; Jonathan C. Lovely

(57) ABSTRACT

A medical port has a housing forming an interior with a fluid inlet and a fluid channel extending from the fluid inlet. The housing also has an exterior wall forming at least one radial opening to the interior. In addition to the housing, the medical port also has a resilient valve element within the housing interior configured to control fluid flow through the inlet, and a biasing element movably couplable with the housing. The resilient valve element has a proximate body portion proximate to the radial opening when in the closed mode. The biasing element also has a constraining portion configured to cooperate with the radial opening to contact at least the proximate body portion of the valve element when in the closed mode. The biasing element constraining portion preferably is configured to normally resist radial outward movement of the proximate body portion when in the closed mode.

20 Claims, 11 Drawing Sheets

(51) Int. Cl.
*A61M 39/04* (2006.01)
*A61M 39/22* (2006.01)
*A61M 39/26* (2006.01)
*A61M 39/00* (2006.01)

(52) U.S. Cl.
CPC .... *A61B 5/15003* (2013.01); *A61B 5/150328* (2013.01); *A61B 5/150992* (2013.01); *A61M 39/04* (2013.01); *A61M 39/045* (2013.01); *A61M 39/223* (2013.01); *A61M 39/26* (2013.01); *A61M 2039/0072* (2013.01)

(56) References Cited

U.S. PATENT DOCUMENTS

| | | | |
|---|---|---|---|
| 5,203,771 | A | 4/1993 | Melker et al. |
| 5,221,271 | A | 6/1993 | Nicholson et al. |
| 5,354,275 | A | 10/1994 | Behnke et al. |
| 5,360,413 | A | 11/1994 | Leason et al. |
| 5,417,673 | A | 5/1995 | Gordon |
| 6,089,541 | A | 7/2000 | Weinheimer et al. |
| RE37,357 | E | 9/2001 | Lynn |
| 7,314,061 | B2 | 1/2008 | Peppel |
| 7,314,452 | B2 | 1/2008 | Madonia |
| 7,556,060 | B2 | 7/2009 | Guala |
| 7,984,730 | B2 | 7/2011 | Ziv et al. |
| 8,568,371 | B2* | 10/2013 | Siopes ............ A61M 39/26 604/256 |
| 9,079,005 | B2 | 7/2015 | Chelak et al. |
| 2005/0261637 | A1 | 11/2005 | Miller |
| 2006/0213563 | A1 | 9/2006 | Peppel |
| 2006/0217671 | A1 | 9/2006 | Peppel |
| 2007/0093762 | A1* | 4/2007 | Utterberg ............ A61M 39/02 604/256 |
| 2007/0260195 | A1 | 11/2007 | Bartholomew et al. |
| 2011/0308651 | A1 | 12/2011 | Ziv et al. |
| 2015/0112271 | A1 | 4/2015 | Chelak et al. |

FOREIGN PATENT DOCUMENTS

| | | |
|---|---|---|
| WO | WO 2006/052655 | 5/2006 |
| WO | WO 2008/101025 A1 | 8/2008 |
| WO | WO 2015/100135 | 7/2015 |

OTHER PUBLICATIONS

International Searching Authority, International Search Report—International Application No. PCT/US2017/065944, dated Apr. 9, 2018 together with the Written Opinion of the International Searching Authority, 12 pages.

* cited by examiner

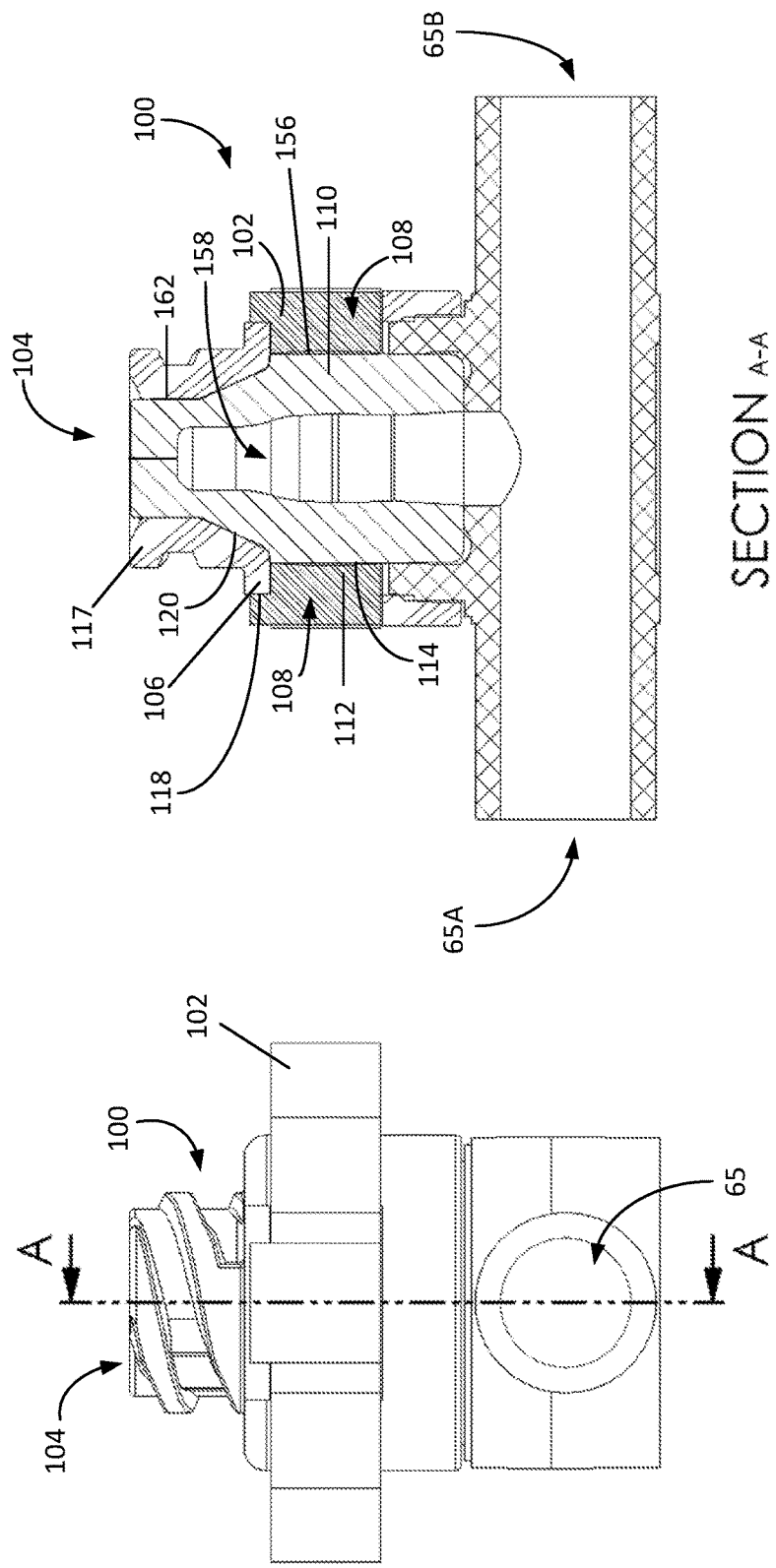

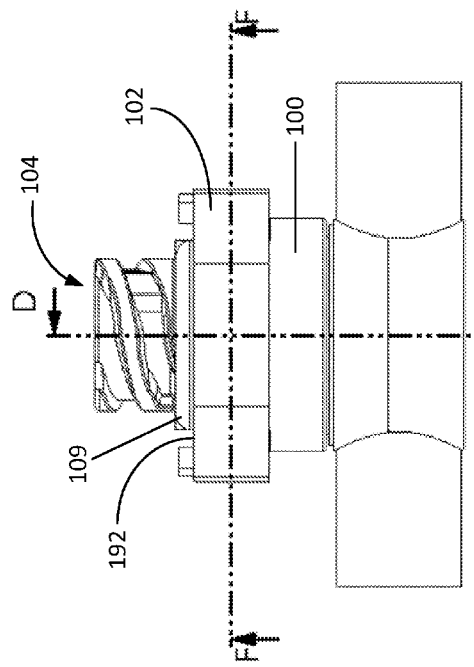
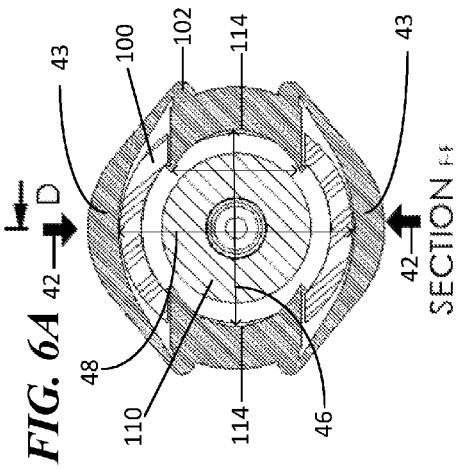
FIG. 5A
FIG. 5B
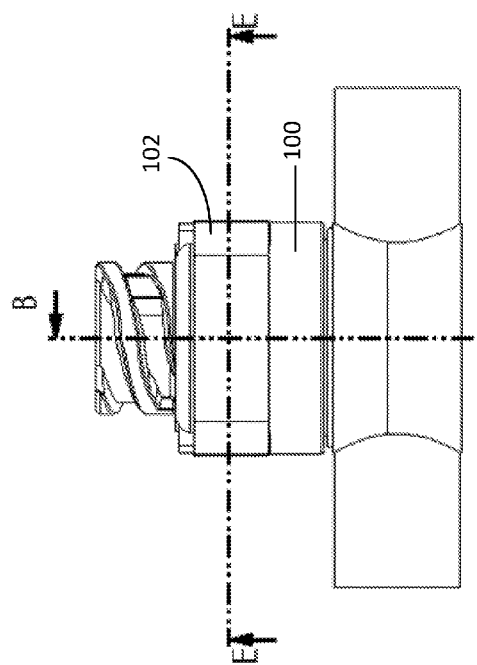
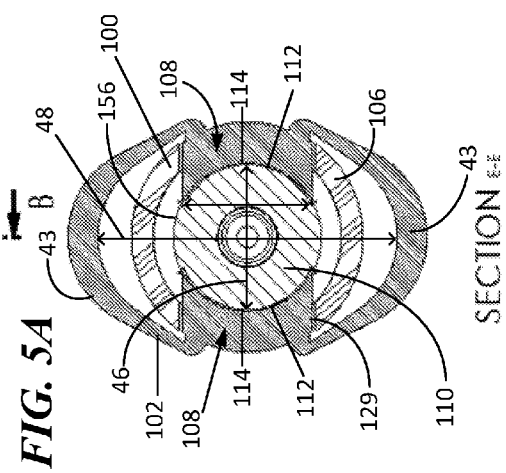
FIG. 6A
FIG. 6B

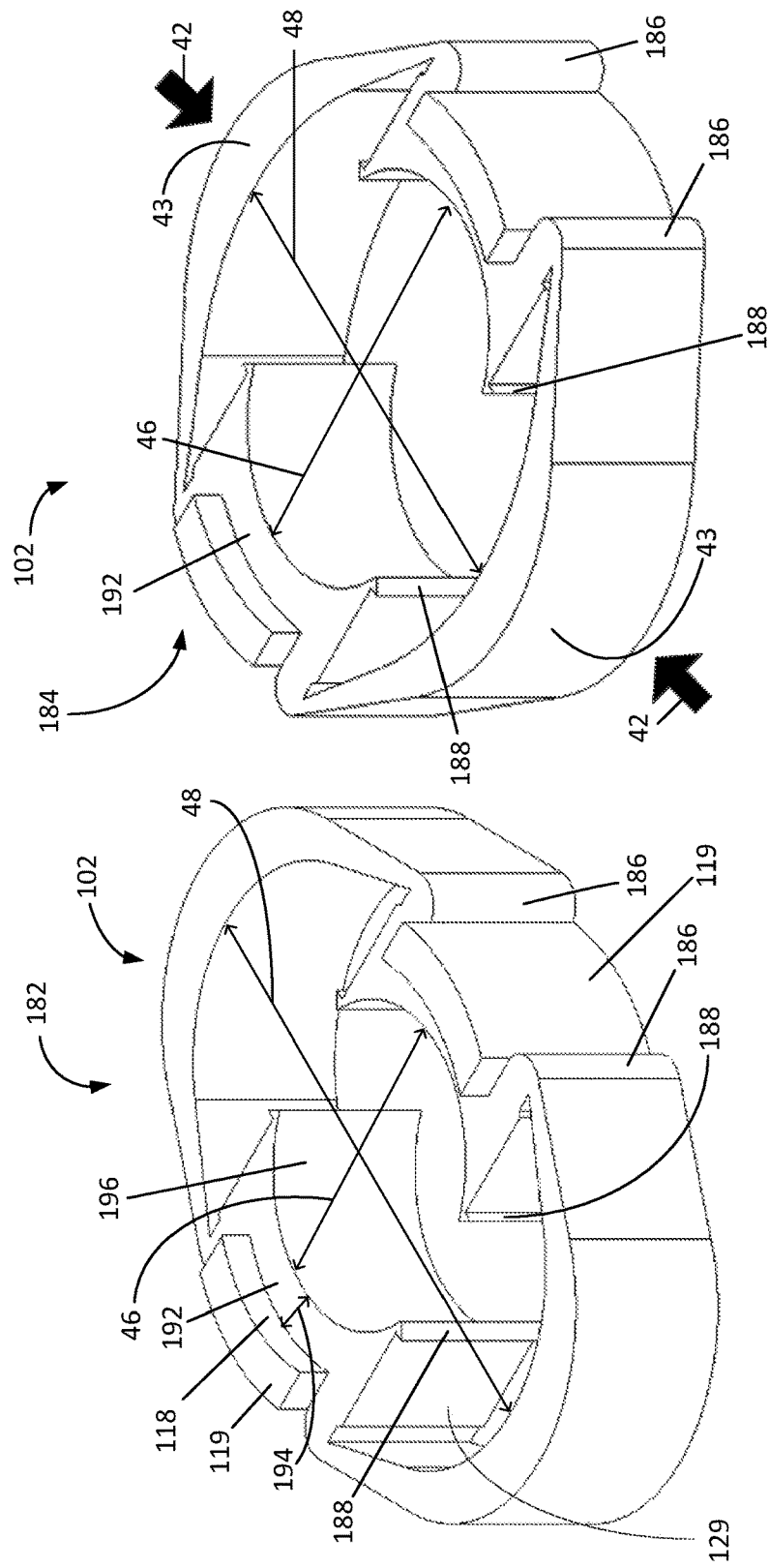

MEDICAL PORT WITH CONSTRAINING BIASING ELEMENT

FIELD OF THE INVENTION

Various embodiments of the invention generally relate to fluid delivery and medical porting devices and, more particularly, the various embodiments of the invention relate to sample ports within arterial or venous fluid transfer and pressure monitoring sets.

BACKGROUND OF THE INVENTION

Many patient fluid transfer applications require a medical practitioner to take a sample of blood or fluid from the patient through an indwelling catheter. To that end, the practitioner typically uses a fluid transfer set having a sample port that allows the medical practitioner to draw a sample of the blood or fluid from the patient's indwelling catheter.

In some critical care applications, the medical practitioner may regularly monitor the patient's arterial blood or venous pressure through the fluid transfer set. In such applications, the fluid transfer set can include a pressure transducer that connects to a display that graphically shows a read-out of the arterial or venous blood pressure. Undesirably, the sampling ports of prior art fluid transfer sets can negatively interfere with the pressure transducer, causing erroneous blood pressure read-outs.

SUMMARY OF VARIOUS EMBODIMENTS

In accordance with one embodiment of the invention, a medical port for transferring fluid to/from a patient functions in an open mode to permit fluid flow and in a closed mode to prevent fluid flow. Among other things, the medical port has a housing forming an interior with a fluid inlet and a fluid channel extending from the fluid inlet. The housing also has an exterior wall forming at least one radial opening to the interior. In addition to the housing, the medical port also has a resilient valve element within the housing interior configured to control fluid flow through the inlet, and a biasing element movably couplable with the housing. The resilient valve element has a proximate body portion proximate to the at least one radial opening when in the closed mode. In a corresponding manner, the biasing element has at least one constraining portion configured to cooperate with the at least one radial opening to contact at least the proximate body portion of the valve element when in the closed mode. The at least one constraining portion preferably is configured to normally resist radial outward movement of the proximate body portion when in the closed mode.

The biasing element may take on a variety of forms. For example, the biasing element may include a closed top portion to substantially cover the fluid inlet when the at least one constraining portion contacts the proximate body portion. Thus, the biasing element may form a cap. Alternatively, the biasing element may allow access to the fluid inlet of the housing when the at least one constraining portion contacts the proximate body portion.

The stiffness of the biasing element and the valve element are coordinated to ensure prescribed results. For example, the biasing element may have a first stiffness, while the resilient valve element may have a second stiffness that is less than or equal to the first stiffness. Moreover, the resilient valve element may have a first portion that abuts the interior of the housing in the closed mode. In that case, the interior of the housing may constrain radial (outward) movement of the first portion in the closed mode, and the proximate body portion may be unconstrained by the housing when in the closed mode.

Illustrative embodiments form the housing and resilient valve element as a sample port. In addition or alternatively, the biasing element may be radially movably coupled with the housing. For example, the biasing element may include a living hinge and a longest distance. The biasing element may be configured to pivot at the living hinge in response to a radially inwardly directed force applied to the longest distance.

The biasing element may be formed from a resilient material that includes at least one stop surface for contacting the housing exterior wall to limit the radial contraction of the biasing element when in the closed mode. The stop surface may be movably adjustable and configured to vary the limit. To improve performance, the at least one constraining portion may be configured to contact between about 180 and 340 degrees of the circumference of the resilient valve element when in the closed mode. To that end, the biasing element may include a plurality of constraining portions that form between two and ten constraining surfaces. The constraining surfaces may be spaced apart around the circumference of the resilient valve element.

In accordance with another embodiment, a medical port for transferring fluid to/from a patient functions in an open mode to permit fluid flow and in a closed mode to prevent fluid flow. Among other things, the medical port has a housing forming an interior with a fluid inlet and a fluid channel extending from the fluid inlet. The housing also has an exterior. The medical port also has a resilient valve element within the housing interior configured to control fluid flow through the inlet, and a biasing element removably couplable with the housing exterior. The resilient valve element has a radially unconstrained valve portion when in the closed mode. In a corresponding manner, the biasing element has at least one constraining portion configured to contact at least a given portion of the radially unconstrained valve portion when the biasing element is coupled with the housing exterior. Accordingly, the at least one constraining portion is configured to normally resist radial outward movement of at least the given portion of the radially unconstrained valve portion when the biasing element is coupled with the housing exterior.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 4A schematically shows a front view of the medical port and the biasing element of FIG. 3B, in accordance with illustrative embodiments of the invention.

FIG. 4B schematically shows a cross-sectional side view of the medical port and the biasing element shown in FIG. 4A along line A-A, in accordance with illustrative embodiments of the invention.

FIG. 5A schematically shows a side view of the biasing element in a constraining state with the medical port, in accordance with illustrative embodiments of the invention.

FIG. 5B schematically shows a cross-sectional bottom view of the biasing element and the medical port shown in FIG. 5A along line E-E, in accordance with illustrative embodiments of the invention.

FIG. 6A schematically shows a side view of the biasing element in a unconstrained state with the medical port, in accordance with illustrative embodiments of the invention.

FIG. 6B schematically shows a cross-sectional bottom view of the biasing element and the medical port shown in FIG. 5A along line F-F, in accordance with illustrative embodiments of the invention.

FIG. 7 schematically shows a perspective view of the biasing element in a free state, in accordance with illustrative embodiments of the invention.

FIG. 8 schematically shows a perspective view of the biasing element in a flexed state, in accordance with illustrative embodiments of the invention.

DESCRIPTION OF ILLUSTRATIVE EMBODIMENTS

In illustrative embodiments, a biasing element movably couples with a medical port having a valve element to ensure that a sensor accurately receives a bio-signal generated by a patient. For example, the medical port may be in-line with a pressure sensor that measures the patient's arterial or venous pressure waveform. Undesirably, some prior art medical ports distort pressure waveform measurements. To overcome that problem, the biasing element constrains at least a portion of the valve element, thus enabling the pressure sensor to make more accurate pressure waveform measurements. Details of illustrative embodiments are discussed below.

Figure 1:
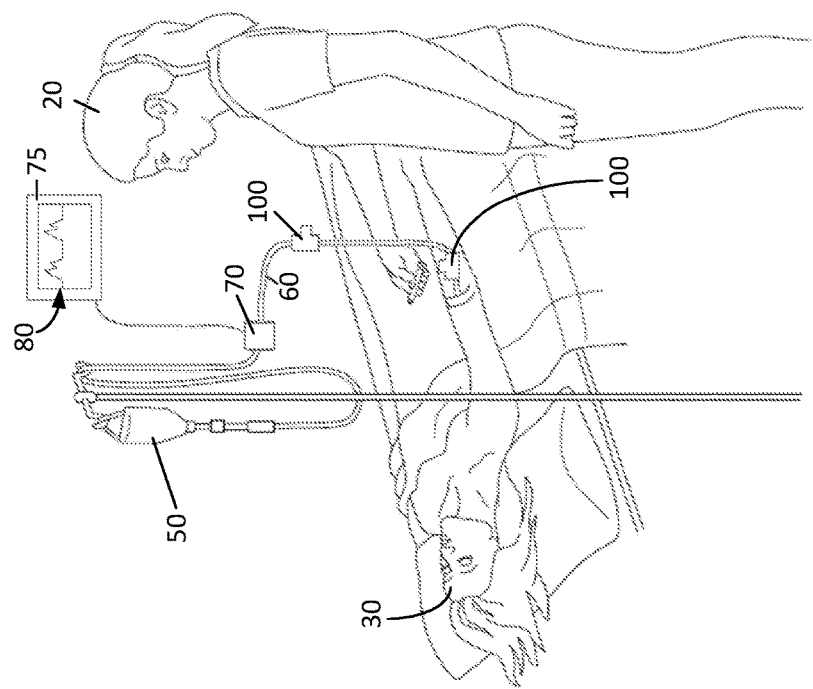
FIG. 1 schematically shows use of a medical port in-line with a pressure transducer, in accordance with illustrative embodiments of the invention.

FIG. 1 schematically shows use of a medical port 100 in-line with a pressure transducer 70, in accordance with illustrative embodiments of the invention. The medical port 100 may be connected to a section of tubing 60. For example, the medical port 100 may be part of a fluid transfer set used to transfer fluids to a patient 30 and/or draw blood from the patient 30. To that end, the medical port 100 may be connected (e.g., bonded, welded, press-fit, etc.) to a section of tubing 60 that leads to a fluid bag 50.

In some applications (e.g., in critical care applications), the medical practitioner 20 (e.g., the nurse 20) may need to monitor venous or arterial pressure of the patient 30 (e.g., the intra-venous or intra-arterial blood pressure). Therefore, in some instances, the fluid transfer set may also include the pressure transducer 70 (i.e., a sensor) with a strain gauge that measures the pressure waveform within the artery or vein. The pressure is converted to an electrical signal, and the signal is forwarded to a monitor 75. The monitor 75, in turn, may display a graphic 80 representing the intra-arterial or intra-venous blood pressure waveform of the patient 30. A healthcare provider, such as a nurse 20, then may check the patient's 30 blood pressure waveform as a means to assess the status of the patient 30.

Figure 2:
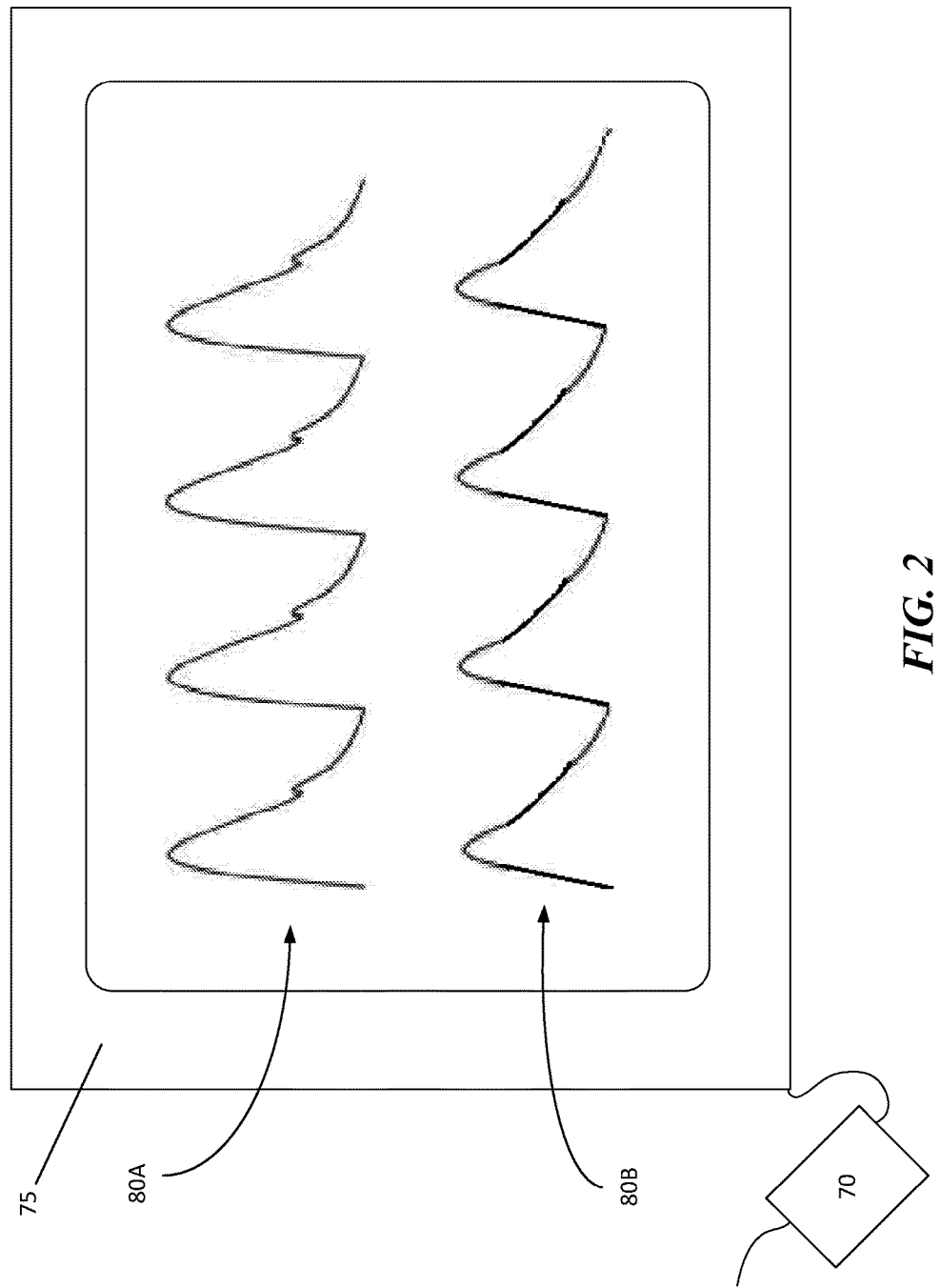
FIG. 2 schematically shows a normal blood pressure reading and a distorted blood pressure reading.

FIG. 2 schematically shows examples of a normal blood pressure waveform reading 80A and a distorted blood pressure waveform reading 80B. Although shown simultaneously in the figure, the monitor 75 generally displays only a single graphic 80 (also referred to as waveform 80). The two different graphics 80A and 80B are shown on the same monitor 75 for convenience. Thus, waveform 80 appears either as normal waveform 80A or as distorted waveform 80B, but not both simultaneously. The graphic 80 is output by the transducer 70, as described above. The inventors discovered that normal blood pressure readings 80A may become distorted blood pressure readings 80B when transducers 70 are in-line with some medical ports 100. To mitigate that problem, illustrative embodiments couple a biasing element 102 to the medical port 100 to significantly mitigate waveform 80 distortion (e.g., the appearance of the waveform 80 as the distorted waveform 80B).

Figure 3B:
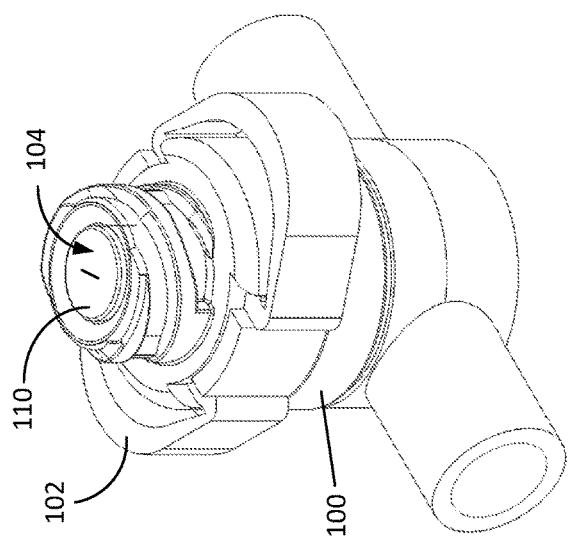
FIGS. 3A-3B schematically show a perspective view of a medical port being used with a biasing element, in accordance with illustrative embodiments of the invention.
Figure 3A:
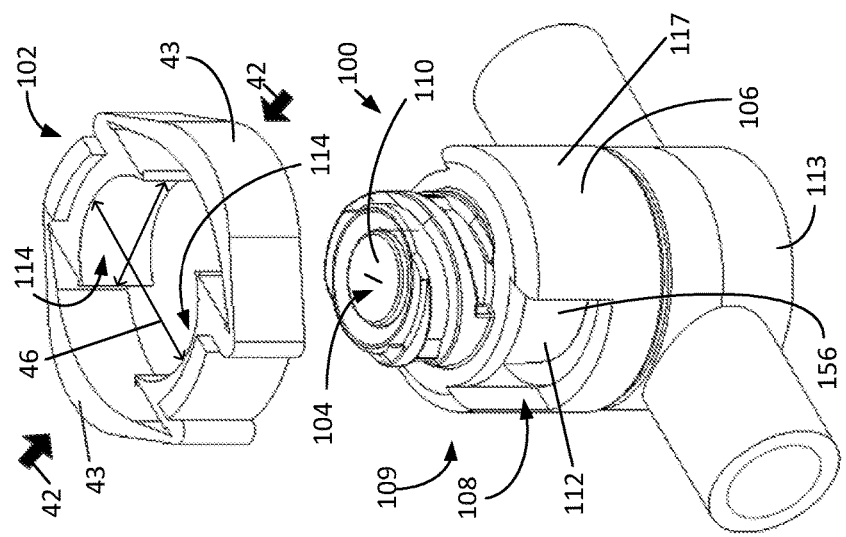

FIGS. 3A-3B schematically show a perspective view of the medical port 100 movably coupling with a biasing element 102, in accordance with illustrative embodiments of the invention. Specifically, FIG. 3A shows the medical port 100 prior to coupling with the biasing element 102. The biasing element 102 is flexible, and in FIG. 3A, flexes so that it may slide onto the medical port 100 (e.g., by assembly equipment grippers or a user at the point of care pressing a squeezing portion 43 of the biasing element 102 in the direction of arrows 42). Flexing the biasing element 102 causes an internal distance 46 of the biasing element 102 to change, and allows the biasing element 102 to fit onto the medical port 100.

The medical port 100, like many medical ports, has a housing 109. The housing 109 may include a distal portion 113 and a proximal portion 117 that, when secured together, form an interior of the housing 109 (e.g., within the interior of a proximal portion 117). To take a fluid sample, the medical port 100 may also include a fluid inlet 104 (e.g., within the proximal portion 117 of the housing 109) capable of receiving a medical implement (e.g., a luer, needleless syringe, blunt cannula, etc.) that can be used to draw a sample from the medical port 100. The medical port 100 also has an elastomeric valve element 110 within the interior of the housing 109 to seal the fluid inlet 104. The biasing element 102 may be shaped as a ring that exposes the fluid inlet 104 while constraining valve element 110 (i.e., while the port 100 is in the closed mode).

The housing 109 has an exterior wall 106 with at least one radial opening 108. The radial opening 108 forms a passage through which a constraining portion 114 of the biasing element 102 may contact, and thus constrain, the valve element 110. As shown, the medical port 100 has two radial openings 108, and the biasing element 102 has two corresponding constraining portions 114. FIG. 3A shows that the valve element 110 has portions adjacent to the radial openings 108. Each of those portions is referred to as "radially unconstrained valve wall 156"

FIG. 3B shows the medical port 100 coupled with the biasing element 102, in accordance with illustrative embodiments of the invention. The valve element 110 may be formed from an elastomeric material, for example, low durometer silicone. The elastomeric valve element 110 may over damp the resonant frequency of the system, leading to waveform 80 distortion as the system frequency approaches the frequencies making up the pressure waveform 80. The inventors discovered that constraining the valve element 110 has the effect of making the valve element 110 more rigid, and thus, reduces the dampening effect on the pressure waveform 80 (i.e., increases the natural frequency of the system above the frequencies making up the pressure waveform 80). Accordingly, the biasing element 102 slides down over the fluid inlet 104, and constrains (e.g., compresses) the valve element 110. Specifically, the constraining portion 114 constrains at least a proximate body portion 112 (shown in FIG. 3A) of the valve element 110. Constraining the proximate body portion 112 reduces waveform 80 distortions that might otherwise appear in the patient's 30 pressure waveform 80 reading.

FIG. 4A schematically shows a front view of the medical port 100 and biasing element 102 of FIG. 3B, in accordance with illustrative embodiments of the invention. As shown, the biasing element 102 movably couples with the medical port 100. In addition to the fluid inlet 104, the medical port 100 has openings/ports 65 that are normally in-line with the tubing 60. The openings 65 are identified by reference numbers 65A and 65B as best seen in FIG. 4B.

FIG. 4B schematically shows a cross-sectional side view of the medical port 100 and the biasing element 102 shown in FIG. 4A along line A-A, in accordance with illustrative embodiments of the invention. Fluid openings 65A and 65B are normally connected in-line with, for example, the patient 30 and the pressure transducer 70, respectively, best shown in FIG. 1. As shown in the cross-section, the valve element 110 has a valve interior that forms a fluid channel 158, through which a sample may be drawn.

As described above, the constraining portion 114 of the biasing element 102 passes through the radial opening 108 in the exterior wall 106 to constrain the proximate body portion 112. The amount of pressure applied by the constraining portion 114 may be determined by, among other things, the physical distances of the biasing element 102. Additionally, the biasing element 102 may have at least one stop surface 118 configured to interact with a surface of the medical port 100 (e.g., the proximal portion 117 of the housing 109). The at least one stop surface 118 provides a physical stop that substantially prevents the constraining portion 114 from applying more pressure to the valve element 110 than desired.

Although the valve element 110 is shown as coupled to the biasing element 102, it should be understood that when the components 110 and 102 are uncoupled, the valve wall 156 is generally unconstrained in the closed mode. By contrast, an inner surface 162 of the housing 109 constrains portions of the valve element 110 in both modes.

Figure 4C:
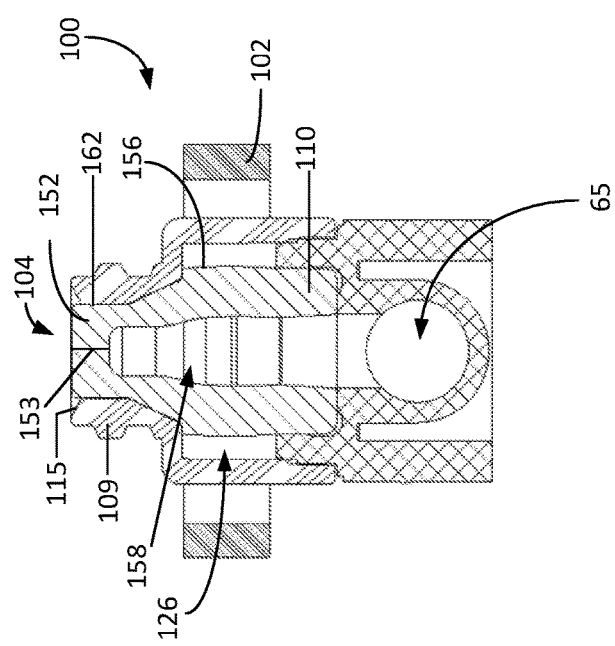
FIG. 4C schematically shows a cross-sectional front view of the medical port and biasing element shown in FIG. 4A, in accordance with illustrative embodiments of the invention.

FIG. 4C schematically shows another cross-sectional front view of the medical port 100 and the biasing element 102 shown in FIG. 4A. As mentioned above, the fluid inlet 104 is configured to draw a sample from the valve element 110 interior 158. To that end, the valve element 110 includes a resealable aperture 153 extending through a proximal portion 152 of the valve element 110. Among other things, the aperture 153 may be a pierced hole or a slit. Alternatively, the proximal portion 152 may be molded with the aperture 153.

In some embodiments, the proximal portion 152 of the valve element 110 may be flush with or extend slightly above an exterior proximal opening face 115 of the housing 109 of the medical port 100. The proximal portion 152 of the valve element 110 and the exterior inlet face 115 thus present a swabbable surface, i.e., it may be easily wiped clean with an alcohol swab, for example, or other swab.

When the valve element 110 is in the closed mode (i.e., preventing passage of fluid through the inlet 104), as shown in FIGS. 4A-4C, the aperture 153 may be held closed by the inner surface 162 of the fluid inlet 104. In that case, the inner diameter of the fluid inlet 104 may be smaller than the outer diameter of the proximal portion 152 and thus, the housing 109 (e.g., the portion near the fluid inlet 104) squeezes the aperture 153 closed. Thus, the housing 109 constrains radial movement of the proximal portion 152, but does not constrain radial movement of the proximate body portion 112.

Alternatively, the valve element 110 (e.g., the proximal portion 152) may be formed so that the aperture 153 normally stays closed in the absence of radially inward force provided by the inner surface 162 of the fluid inlet 104. In other words, the proximal portion 152 may be formed so that the aperture 153 normally is closed. Although the valve element 110 is described as preventing passage of fluid in the closed mode, it should be understood that the term "preventing" is in accordance with the normal use of the valve element 110. A medical practitioner 20 inserting the medical implement, with sufficient force, should deform the elastomeric valve element 110, and thus, allow passage of fluid. It should be understood that the illustrative embodiments may operate with a variety of valve elements 110, and are not limited to the specific valve element 110 shown herein.

During operation (e.g., when taking a sample from the fluid transfer set), the medical practitioner 20 may insert the medical implement into the fluid inlet 104. As the medical implement is inserted, the valve element 110, which normally closes the fluid inlet 104, moves/deforms distally within a valve chamber 126. As the valve element 110 continues to move/deform distally into the valve chamber 126, the aperture 153 opens (e.g., when the proximal portion 152 of the valve element 110 enters the larger inner diameter portion of the proximal portion 117 of the housing 109) to fluidly communicate the medical implement and the valve interior 158. Conversely, when the medical implement is withdrawn from the fluid inlet 104 (e.g., after sampling is complete), the elastomeric properties of the valve element 110 cause the valve element 110 to move proximally within the valve chamber 126 and return to its at-rest position with the proximal portion 152 at least partially within (and closing) the fluid inlet 104.

Although not visible in the cross-section of FIG. 4C, the biasing element 102 contacts and may constrict at least a portion of the valve wall 156. Specifically, as described above, the constraining portion 114 of the biasing element 102 constrains at least a portion of the proximate body portion 112 of the valve element 110. Thus, when coupled, the biasing element 102 inhibits deformation of the valve element 110, and may hinder the medical port 100 from transitioning to the open mode. Alternatively, the biasing element 102 may prevent deformation of the valve element 110. This should not impede waveform 80 monitoring (i.e., waveforms 80 produced by transducer 70), however, which preferably occurs when the medical port 100 is in the closed mode.

FIG. 5A schematically shows a side view of the biasing element 102 when constraining the valve element 110. The constraining portion 114 thus contacts and may compress the proximate body portion 112 of the valve element 110 (best shown in FIG. 5B).

FIG. 5B schematically shows a cross-sectional bottom view of the biasing element 102 and the medical port 100 shown in FIG. 5A along line E-E. As shown, the exterior wall 106 of the medical port 100 partially circumscribes the valve element 110. Gaps in the exterior wall 106 form the radial openings 108 through which the constraining portion(s) 114 of the biasing element 102 pass. After the constraining portion 114 passes through the radial opening 108, the assembly equipment grippers or user may stop inwardly pressing on the squeezing portions 43 to allow the biasing element 102 to travel towards the free state 182. The biasing element 102 may have a distance 46 between the constraining portions 114 (referred to as distance 46) and a distance between the squeezing portions 43 (referred to as distance 48). When the distance 46 becomes larger, the inversely related distance 48 becomes smaller, and vice-versa. Additionally, when the distance 46 becomes smaller, the inversely related distance 48 becomes larger, and vice-versa.

It should be understood that the biasing element 102 may have certain alternative shapes (e.g., hexagonal or decagonal shape), as well as alternative living hinge designs that result in different relationships between constraining portions 114 when in the flexed state 184 and the free state 182. Furthermore, the corresponding forces acting upon portions 43 of the biasing element 102 may be in different directions other than radially inwardly (e.g., outwardly). Furthermore, it should be understood that squeezing portions 43 do not necessarily have to be squeezed. The name "squeezing portions" is used for the ease of understanding illustrative embodiments. Other illustrative embodiments having portions 43 may be pressed outwardly rather than squeezed together.

When the biasing element 102 unflexes (as it does when at rest and not coupled with the medical port 100), the distance 46 between the constraining portions 114 is at a natural minimum—its normal position. In other words, the distance 46 does not decrease further, absent the application of some outside force. Furthermore, when the distance 46 decreases, the inversely related distance 48 may increase. Thus, when the biasing element 102 unflexes, the distance 46 between the constraining portions 114 is minimized, and compression on the valve element 110, specifically the proximate body portion 112, is maximized. It should be understood, however, that the biasing element 102 may not reach a fully unflexed state, when coupled to the medical port 100, because of removable connection/interference fit of the valve element 110 between the constraining portions 114.

In some embodiments, the biasing element 102 does not completely unflex when coupled with the medical port 100 because the stop surface 118 (see FIG. 4B) prevents the biasing element 102 from unflexing, and thus, prevents the distance 46 from decreasing beyond some set distance value. Additionally, or alternatively, the interaction of a sidewall 129 of the constraining portion 114 and the exterior wall 106 may prevent the biasing element 102 from fully unflexing, and thus, prevent distance 46 from decreasing beyond some set value. As the distance 46 decreases, the distance 48 increases, and thus, the distance 48 is also prevented from reaching its maximum length. Accordingly, the biasing element 102 and the medical port 100 may be manufactured to provide the desired amount of compression on the valve element 110 in the coupled state including line-to-line contact (e.g., by controlling the distance 46 via the use of stop surfaces 118 and the interaction of the exterior wall 106 and the sidewall 129). Some embodiments, however, do not use the stop surface 118 and/or sidewall 129.

Although illustrative embodiments are described as having two constraining portions 114, it should be understood that more than two constraining portions 114 (e.g., one or more) may be used. In preferred embodiments, the constraining portion(s) 114 contact, in total, between about 180 and 340 degrees of the circumference of the valve element 110 while constraining the valve wall 156. However, the inventors have found that as little as 30 degrees of radial compression on two sides (i.e., 60 degrees in total) may reduce waveform 80 distortion. Thus, for example, the biasing element 102 may have three equidistant constraining portions 114 that each contact approximately 60 degrees of the circumference of the valve element 110. Alternatively, the biasing element 102 may have four equidistant constraining portions 114 that each contact approximately 60 degrees of the circumference of the valve element 110.

A person of skill in the art knows how to select and orient an appropriate number and arc length (in degrees) of constraining portions 114. For example, the person skilled in the art may model and iteratively test an appropriate arc length. Furthermore, it is not necessary that each constraining portion 114 be identical, e.g., each constraining portion 114 may have a different arc length. Additionally, it is not necessary that the constraining portions 114 be equidistant around the circumference of the valve element 110. The exterior wall 106 may also be configured to have sufficient radial openings 108 to allow for the passage of the requisite number of constraining portions 114. Accordingly, illustrative embodiments have a number of radial openings 108 (e.g., one or more) configured to accept the number and spacing of the constraining portions 114.

FIG. 6A schematically shows a side view of the biasing element 102 when not constraining the medical port 100. FIG. 6B schematically shows a cross-sectional bottom view of the biasing element 102 and medical port 100 shown in FIG. 5A along line F-F, but also when not constraining the medical port 100. Among other ways, a user may unconstrain the biasing element 102 from the medical port 100 simply by pressing the squeezing portions 43 radially inwardly as shown by the arrows 42. Pressing the squeezing portions 43 in this manner decreases the inversely related distance 48, which in turn causes the constraining portions 114 to retract radially outward and increase the distance 46. The constraining portions 114 no longer constrain the valve element 110. Thus, the medical practitioner 20 may now insert a medical implement into the inlet 104 without resistance from the biasing element 102 and draw a sample. The valve element 110, which is no longer constrained, moves/deforms distally and radially outward within a valve chamber 126 (see FIG. 4C). As the valve element 110 or more specifically, the proximal portion 152, continues to move distally towards the valve chamber 126, the aperture 153 opens, and a sample may be drawn.

In some embodiments at least part of the constraining portions 114 move radially outward and clear the overhead housing 109 (shown in FIG. 6A). The radially outward movement may provide radial clearance between the biasing element 102, e.g., top surface 192, and the housing 109. Thus, the medical practitioner 20 may now slide the biasing element 102 proximally past the fluid inlet 104 to uncouple the biasing element 102 and the medical port 100. However, in some embodiments the housing 109 still at least partially covers the constraining portion 114 and prevents removal of the biasing element 102.

After the biasing element 102 and the medical port 100 are uncoupled, a practitioner 20 may insert a medical instrument through the fluid inlet 104. To recouple the biasing element 102 and the medical port 100, the user presses on the squeezing portion 43, aligns the central axis of medical port 100 and the biasing element 102 (e.g., line D-D), and slides the biasing element 102 down over the fluid inlet 104. After the user stops pressing on the squeezing portions 43, the constraining portions 114 contract radially inwardly to constrain the valve element 110. Accordingly, the biasing element 102 and the medical port 100 are radially movably coupled. In alternative embodiments, the biasing element 102 and the medical port 100 may be permanently coupled, while the biasing element 102 is movably couplable with the valve element 110.

FIG. 7 schematically shows a perspective view of the biasing element 102 in an undeformed free state 182 (i.e., in its normal state), in accordance with illustrative embodiments of the invention. The free state 182 is the configuration of the biasing element 102 at rest and may be similar to, or the same as, the biasing element 102 constraining state. However, as discussed above, illustrative embodiments are not in the free state 182 when coupled to the medical port 100 because of, among other things, the stop surface 118.

FIG. 8 schematically shows a perspective view of the biasing element 102 in a flexed state 184, in accordance with illustrative embodiments of the invention. When the user radially inwardly presses the squeezing portions 43, as shown by the arrows 42, the biasing element 102 is in the flexed state 184. Hinges 186 connected to the squeezing portion 43 flex to accommodate the pressure, and thus distance 48 decreases. As the distance 48 decreases, the distance 46 correspondingly increases 46. The increased distance 46 provides radial clearance between the biasing element 102, e.g., top surface 192, and the housing 109 of the medical port 100. The hinge 186 may be a living hinge 186, e.g., the hinge 186 may be formed from the same material as the rest of the biasing element 102. Alternatively, the biasing element 102 may be formed from more than one material having different mechanical properties to achieve different zones and degrees of flexibility/rigidity.

In some embodiments, the biasing element 102 may be non-removably coupled to the medical port 100. To that end, hooks 188 may be used to contact and retain the inner diameter of the exterior wall 106 of the medical port housing 109. In such embodiments, although the biasing element 102 and medical port 100 may still be coupled and uncoupled during use (e.g., in a constraining state and an unconstrained state, respectively), the hooks 188 prevent removal of the biasing element 102 from the medical port 100. Alternatively, some embodiments may be removably coupled to the medical port 100.

A stop member 119 has the stop surface 118 that interacts with the housing 109 to control the distance 46, and thus, the amount of compression applied on the valve element 110. The interference fit between the biasing element 102 and the valve element 110 is controlled by, among other things, the dimensions and thickness of the stop member 119. For example, a clearance 194 may exist between the stop surface 118 and a constraining surface 196 of the constraining portion 114. As the clearance 194 becomes smaller, the stop surface 118 comes closer to the housing 109. Thus, the stop surface 118 contacts the housing 109 earlier than it otherwise would if the clearance 194 was larger. Accordingly, in illustrative embodiments the distance 46 in the constraining state is at least partially dictated by the clearance 194 of the stop surface 118. In some embodiments, at least a portion of the stop member 119 is movably adjustable (e.g., slideable), and thus, the clearance 194 may be adjustable.

Figure 9B:
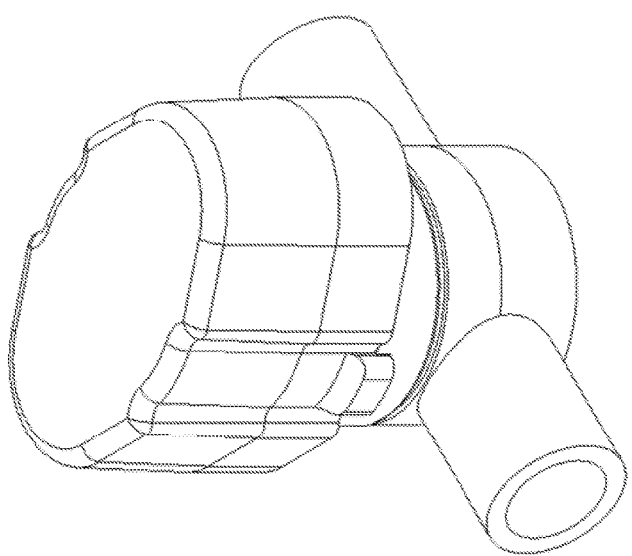
FIGS. 9A-9B schematically show a perspective view of a medical port being used with an alternative embodiments of the biasing element, in accordance with illustrative embodiments of the invention.
Figure 9A:
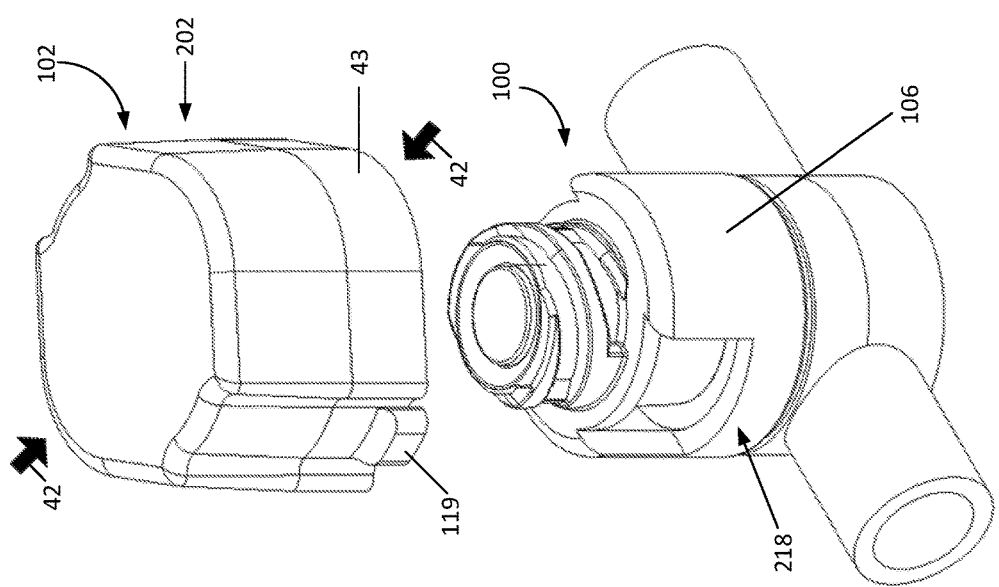

FIGS. 9A-9B schematically show a perspective view of the medical port 100 being used with an alternative embodiment of the biasing element 102. As shown, the biasing element 102 is generally integrated into a conventional disinfecting cap 202. This embodiment operates in a similar manner to the embodiment shown in FIGS. 3A-3B. To that end, the cap 202 has the squeezing portion 43 that the user presses in the direction of the arrows 42. Squeezing the cap 202 radially inwardly causes a change in the internal distances 46 and 48, similar to those described above, which allows the cap 202 to slide over and couple with the medical port 100.

In illustrative embodiments, the cap 202 has the stop member 119 on a bottom surface that interacts with a cap contact surface 218 of the exterior wall 106. As described above, the stop member 119 may be shaped and sized in various ways to control the amount of compression on the valve element 110.

Figure 10:
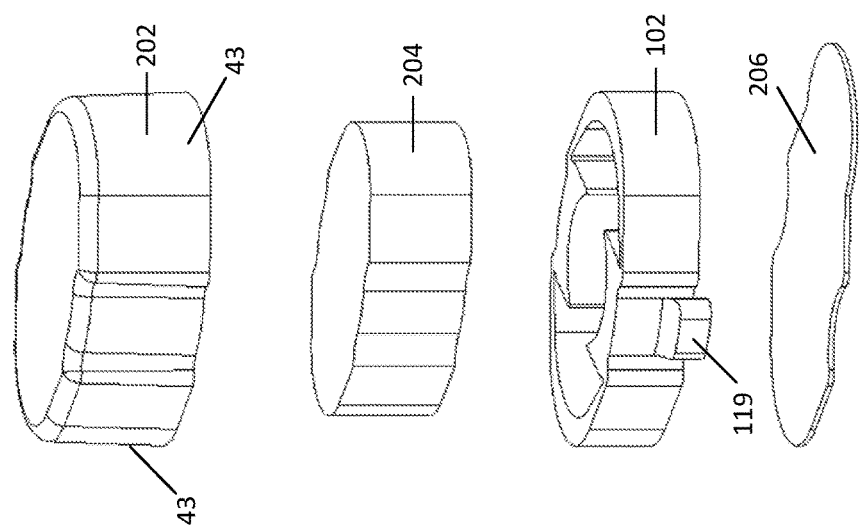
FIG. 10 schematically shows an exploded view of a disinfecting cap containing the biasing element shown in FIGS. 9A-9B, in accordance with illustrative embodiments of the invention.

FIG. 10 schematically shows an exploded view of the disinfecting cap 202, containing the biasing element 102, shown in FIGS. 9A-9B. The cap 202 may have some features similar to a conventional disinfecting cap known in the art. Moreover, the cap 202 may include a sponge/ disinfecting pad 204 saturated with a cleaning agent, such as isopropyl alcohol. The sponge 204 releases isopropyl alcohol when it is coupled to and compressed by the medical port 100.

The biasing element 102 may surround the sponge 204 inside the cap 202. Alternatively, the biasing element 102 may form the bottom of the cap 202 and partially enclose the sponge 204 therein. The biasing element 102 operates as described above. Illustrative embodiments may position the stop member 119 at the bottom of the biasing element 102, as shown, or at the top as shown in other illustrative embodiments. The cap 202 may also come assembled with a peel off liner 206 that maintains the sterility of the cap 202 prior to use. To use the cap 202, the practitioner 20 peels off the liner 206, radially inwardly presses the squeezing portion 43 of the cap 202, and slides the cap 202 onto the medical port 100. Alternatively, the cap 202 may be pressed downwardly and/or rotationally upon the medical port 100 to cam the constraining portion 114 outwardly and automatically move the squeezing portion 43 inwardly.

Figure 11B:
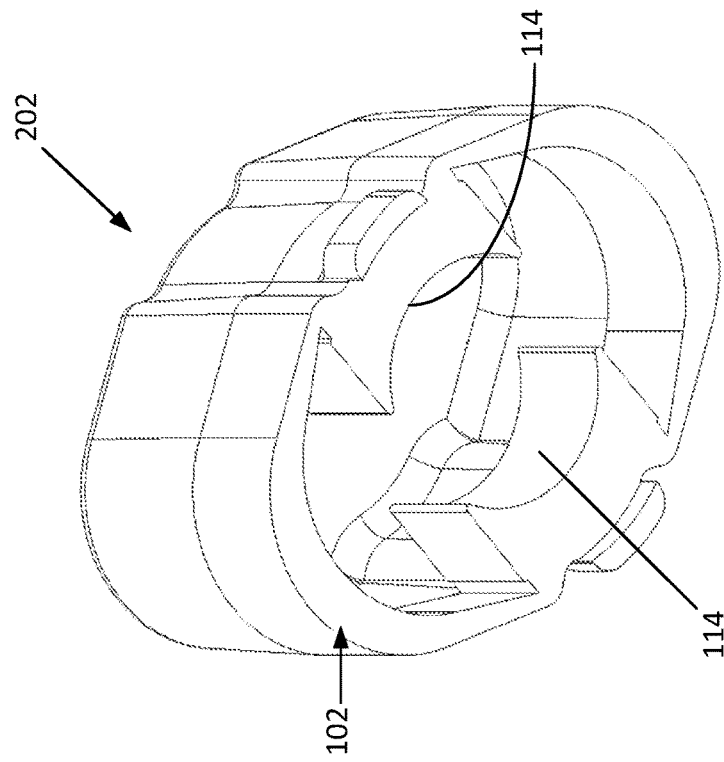
FIG. 11B schematically shows a bottom perspective view of the biasing element shown in FIGS. 9A-9B, in accordance with illustrative embodiments of the invention.
Figure 11A:
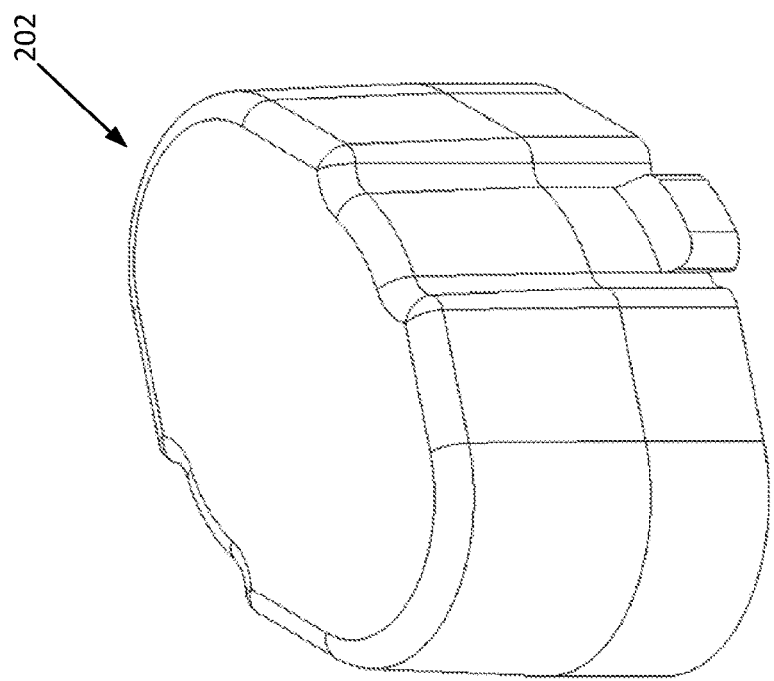
FIG. 11A schematically shows a top perspective view of the biasing element shown in FIGS. 9A-9B, in accordance with illustrative embodiments of the invention.

FIG. 11A schematically shows a top perspective view of the cap 202 shown in FIGS. 9A-9B. FIG. 11B schematically shows a bottom perspective view of the cap 202 shown in FIGS. 9A-9B. Similar to prior discussed embodiments, the biasing element 102 contacts and may compress the proximate body portion 112 of the valve element 110. In illustrative embodiments, the biasing element 102 is formed as a unitary structure with the cap 202. In alternative embodiments, the biasing element 102 may be configured to attach to standard disinfecting cap structures without the peel off liner 206. In some embodiments, it may be desirable to remove the cap 202 from the medical port 100 during use, such as to draw a sample. To that end, hooks 188 may be removed from the biasing element 102 to facilitate ease of uncoupling.

At least a portion of the biasing element 102 may be formed of the same material as the cap 202. In some embodiments, at least a portion of the biasing element 102 is molded into the structure of the cap 202. Alternatively, the baising element 102 may be formed of different material from the cap 202. The biasing element 102 may be formed from, for example, semi-rigid thermoplastics such as polyethylene or polypropylene. Alternatively, at least a portion of the biasing element 102 may be formed from high-durometer elastomers. At least a portion of the biasing element 102 may be manufactured as an overmolded structure to the cap 202, e.g., a high-durometer elastomer overmolding a semi-rigid thermoplastic.

Figures 12A, 12B:
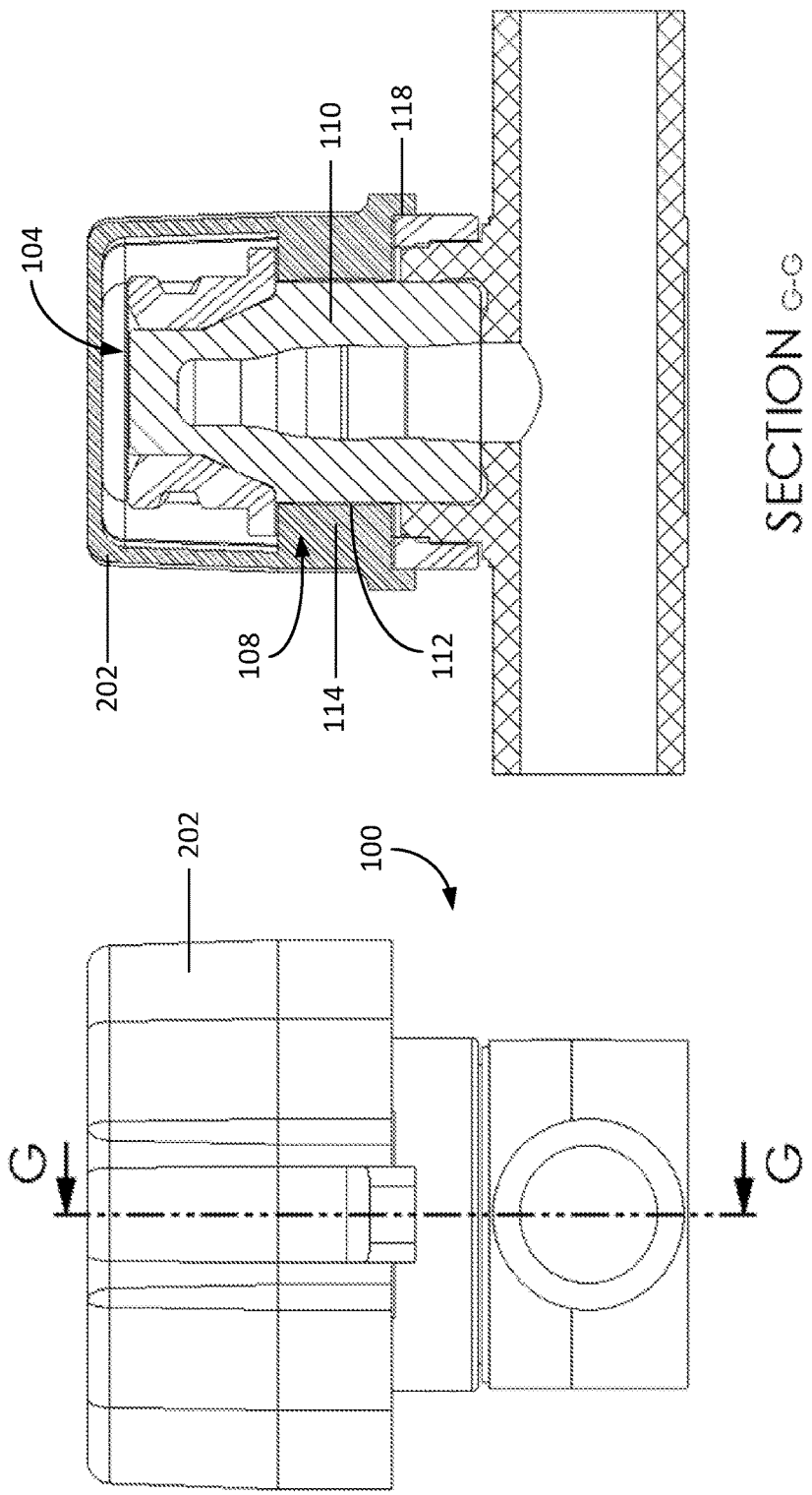
FIG. 12A schematically shows a front view of the medical port and biasing element of FIGS. 9A-9B, in accordance with illustrative embodiments of the invention.
FIG. 12B schematically shows a cross-sectional side view of the medical port and biasing element shown in FIG. 12A along line G-G, in accordance with illustrative embodiments of the invention.

FIG. 12A schematically shows a front view of the cap 202 and the medical port 100 of FIGS. 9A-9B. FIG. 12B schematically shows a cross-sectional side view of the cap 202 and the medical port 100 shown in FIG. 12A along line G-G. The cap 202 has a closed top portion that substantially covers the fluid inlet 104. As described above, the medical port 100 has radial openings 108 through which constraining portions 114 of the cap 202 are able to pass. The constraining portions 114 compress at least the proximate body portion 112. The cap 202 may also have the stop surface 118 to control the amount of compression on the valve element 110.

Advantages of illustrative embodiments of the invention include mitigation of artifacts and/or noise in waveforms 80 created by pressure transducers 70 that are caused by in-line medical ports 100. To that end, illustrative embodiments of the invention provide movably couplable biasing elements 102. As a further advantage, medical practitioners 20 may keep medical ports 100 in-line with the pressure transducer 70 while taking reliable waveform 80 pressure measurements. Furthermore, certain illustrative embodiments of the invention offer the advantage of covering and/or disinfecting the fluid inlet 104 to reduce the likelihood of microbial ingress into fluid channel 158 upon inserting a medical implement following cap 202 removal.

Although the above discussion discloses various exemplary embodiments of the invention, it should be apparent that those skilled in the art can make various modifications that will achieve some of the advantages of the invention without departing from the true scope of the invention.

What is claimed is:

1. A medical port for transferring fluid to/from a patient, the medical port having an open mode to permit fluid flow and a closed mode to prevent fluid flow, the medical port comprising: a housing forming an interior having a fluid inlet and a fluid channel extending from the fluid inlet, the housing also having an exterior wall forming at least one radial opening to the interior; a resilient valve element within the housing interior configured to control fluid flow through the inlet, the resilient valve element having a proximate body portion proximate to the at least one radial opening when in the closed mode; and a biasing element movably couplable with the housing, the biasing element having at least one constraining portion extending into and cooperating with the at least one radial opening to contact at least the proximate body portion when in the closed mode, the at least one constraining portion configured to normally resist radial outward movement of the proximate body portion when in the closed mode.

2. The medical port as defined by claim 1 wherein the biasing element comprises a closed top portion to substantially cover the fluid inlet when the at least one constraining portion contacts the proximate body portion, the biasing element forming a cap.

3. The medical port as defined by claim 1 wherein the biasing element allows access to the fluid inlet of the housing when the at least one constraining portion contacts the proximate body portion.

4. The medical port as defined by claim 1 wherein the biasing element includes at least one stop surface configured to contact the housing exterior wall to limit the radial contraction of the biasing element when in the closed mode, the stop surface being movably adjustable and configured to vary the limit.

5. The medical port as defined by claim 1 wherein the resilient valve element has a first portion that abuts the interior of the housing in the closed mode, the interior of the housing constraining radial and/or longitudinal movement of the first portion in the closed mode, the proximate body portion being unconstrained by the housing when in the closed mode.

6. The medical port as defined by claim 1 wherein the housing and the resilient valve element form a sample port.

7. The medical port as defined by claim 1 wherein the biasing element is radially movably coupled with the housing.

8. The medical port as defined by claim 1 wherein the biasing element is formed from a resilient material and includes at least one stop surface that contacts the housing exterior wall to limit the radial contraction of the biasing element when in the closed mode.

9. The medical port as defined by claim 1 wherein the biasing element includes a living hinge and a longest distance, the biasing element being configured to pivot at the living hinge in response to a radially inwardly directed force applied to the longest distance.

10. The medical port as defined by claim 1 wherein the resilient valve element forms a circumference,
the biasing element further comprising a plurality of constraining portions forming between two and ten constraining surfaces, the constraining surfaces being spaced apart around the circumference.

11. A medical port for transferring fluid to/from a patient, the medical port having an open mode to permit fluid flow and a closed mode to prevent fluid flow, the medical port comprising: a housing forming an interior having a fluid inlet and a fluid channel extending from the fluid inlet, the housing also having an exterior wall forming at least one radial opening to the interior; means for controlling fluid flow through the fluid inlet, the fluid controlling means having a proximate portion proximate to the at least one radial opening when in the closed mode; and means for biasing the proximate portion, the biasing means being radially movably couplable with the housing, the biasing means having at least one constraining portion extending into and cooperating with the at least one radial opening to contact at least the proximate portion of the fluid controlling means when in the closed mode, the at least one constraining portion configured to normally resist radial outward movement of the proximate portion of the fluid controlling means when in the closed mode.

12. The medical port as defined by claim 11 wherein the biasing means comprises a cap configured to cover the fluid inlet when in the closed mode.

13. The medical port as defined by claim 11 wherein the biasing means comprises a ring that allows access to the fluid inlet when in the closed mode.

14. The medical port as defined by claim 11 wherein the biasing means includes at least one stop surface configured to contact the housing exterior wall to limit the radial contraction of the biasing element when in the closed mode, the stop surface being movably adjustable and configured to vary the limit.

15. The medical port as defined by claim 11 wherein the fluid controlling means has a first portion that abuts the interior of the housing in the closed mode, the interior of the housing constraining radial and/or longitudinal movement of the first portion in the closed mode, the proximate body portion being unconstrained by the housing when in the closed mode.

16. A medical port for transferring fluid to/from a patient, the medical port having an open mode to permit fluid flow and a closed mode to prevent fluid flow, the medical port comprising:
- a housing forming an interior having a fluid inlet and a fluid channel extending from the fluid inlet, the housing also having an exterior;
- a resilient valve element within the housing interior configured to control fluid flow through the inlet, the resilient valve element having a radially unconstrained valve portion when in the closed mode; and
- a biasing element movably couplable with the housing exterior, the biasing element having at least one constraining portion configured to contact at least a given portion of the radially unconstrained valve portion when the biasing element is coupled with the housing exterior, the at least one constraining portion configured to normally resist radial outward movement of at least the given portion of the radially unconstrained valve portion when the biasing element is coupled with the housing exterior, the biasing element also configured to be decoupled with the housing exterior prior to the medical port being transitioned from the closed mode to the open mode.

17. The medical port as defined by claim 16 wherein the housing exterior forms at least one radial opening, the at least one constraining portion extending through the at least one radial opening to contact the radially unconstrained valve portion when the biasing element is coupled with the housing exterior.

18. The medical port as defined by claim 16 wherein the biasing element includes a closed top portion to form a cap covering the fluid inlet when the biasing element is coupled with the housing exterior.

19. The medical port as defined by claim 18 further comprising a disinfecting pad containing alcohol between the closed top of the biasing element and the fluid inlet when the biasing element is coupled with the housing exterior.

20. The medical port as defined by claim 16 wherein the biasing element forms an interference fit with the housing when coupled with the housing exterior.

* * * * *